| (12) | United States Patent | (10) Patent No.: US 11,020,342 B2 |
|---|---|---|
| | Kurfurst et al. | (45) Date of Patent: Jun. 1, 2021 |

(54) COSMETIC COMPOSITION COMPRISING ROYAL JELLY OF THE OUESSANT BLACK BEE

(71) Applicant: L V M H Recherche, Saint Jean de Braye (FR)

(72) Inventors: Robin Kurfurst, Saint Jean de Braye (FR); Lauren Sobilo, Chanteau (FR); Milene Juan, Saint Jean de Braye (FR); Emmanuelle Leblanc, Saint Denis en Val (FR); Olivier Jeanneton, Vitry aux Loges (FR); Jean-Christophe Archambault, Meung s/Loire (FR)

(73) Assignee: L V M H RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/472,314

(22) PCT Filed: Dec. 22, 2017

(86) PCT No.: PCT/EP2017/084402
§ 371 (c)(1),
(2) Date: Jun. 21, 2019

(87) PCT Pub. No.: WO2018/115448
PCT Pub. Date: Jun. 28, 2018

(65) Prior Publication Data
US 2019/0374460 A1 Dec. 12, 2019

(30) Foreign Application Priority Data
Dec. 22, 2016 (FR) ..................................... 1663154

(51) Int. Cl.
*A61K 8/98* (2006.01)
*A61K 8/06* (2006.01)
*A61Q 19/08* (2006.01)

(52) U.S. Cl.
CPC .............. *A61K 8/988* (2013.01); *A61K 8/062* (2013.01); *A61K 8/064* (2013.01); *A61Q 19/08* (2013.01); *A61K 2800/436* (2013.01); *A61K 2800/522* (2013.01)

(58) Field of Classification Search
None
See application file for complete search history.

(56) References Cited

U.S. PATENT DOCUMENTS

2009/0068128 A1 3/2009 Waddington
2011/0268812 A1 11/2011 Cauchard et al.

FOREIGN PATENT DOCUMENTS

EP 1 438 964 7/2004

OTHER PUBLICATIONS

Peng, C. et al. The Functional Property of Royal Jelly 10-Hydroxy-2-Decanoic Acid as a Melanogenesis Inhibitor. BMC Complementary and Alternative Medicine 17(1)392-400 Aug. 9, 2017. (Year: 2017).*
Viuda-Martos M. et al. Functional Properties of Honey, Propolis, and Royal Jelly. J of Food Science 73(9)R117-124, Nov. 2008. (Year: 2008).*
*Extraordinary Oil-Cream*, http://www.gnpd.com (Apr. 2016).
*Face Treatment Oil*, http://www.gnpd.com (Nov. 2013).
*Gold Eyetech Eye Sculpt*, http://www.gnpd.com (Sep. 2015).
*Rich Day Cream Firming, Wrinkle Minimizing, Radiance* http://www.gnpd.com (Feb. 10, 2016).
*Ultimate Repair Cream*, http://www.gnpd.com (Feb. 3, 2001).
*Youth Serum*, http://www.qnpd.com (Feb. 9, 2010).
Gumez et al., *Molecular structure of tail tendon fibers in TIEG1 knockout mice using synchrotron diffraction technology*, 108 J. App. Physiol. 1706-1710 (2010).
Martin, *Wound Healing—Aiming for Perfect Skin Regeneration*, 276 Science 75-81 (Apr. 4, 1997).
Snyder, *Classification of the Solvent Properties of Common Liquids*, 92 Journal of Chromatography 223-230 (1974).
Subramaniam et al., *Functional role of KLF10 in multiple disease processes*, 36(1) Biofactors 8-18 (2010).
Subramaniam et al., *TIEG1 Null Mouse-Derived Osteoblasts Are Defective in Mineralization and in Support of Osteoclast Differentiation In Vitro*, 25(3) Molecular and Cellular Biology 1191-199 (Feb. 2005).
Taguchi et al., *Wound-Healing Properties of Transforming Growth Factor TGF-β Inducible Early Gene 1 (TIEG1) Knockout Mice*, 11(2) J. Musculoskelet Res. 63-69 (June 1, 2008).

\* cited by examiner

*Primary Examiner* — Ralph J Gitomer
(74) *Attorney, Agent, or Firm* — Panitch Schwarze Belisario & Nadel LLP

(57) ABSTRACT

The invention relates to a cosmetic composition comprising royal jelly of the Ouessant black bee in a cosmetically acceptable medium, and to its use for regenerating and/or healing the skin.

6 Claims, 4 Drawing Sheets

A

Figure 1:
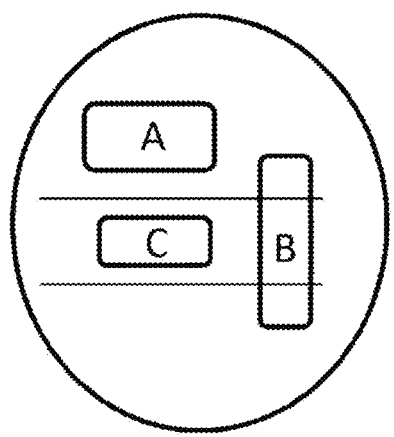
Figure 1:
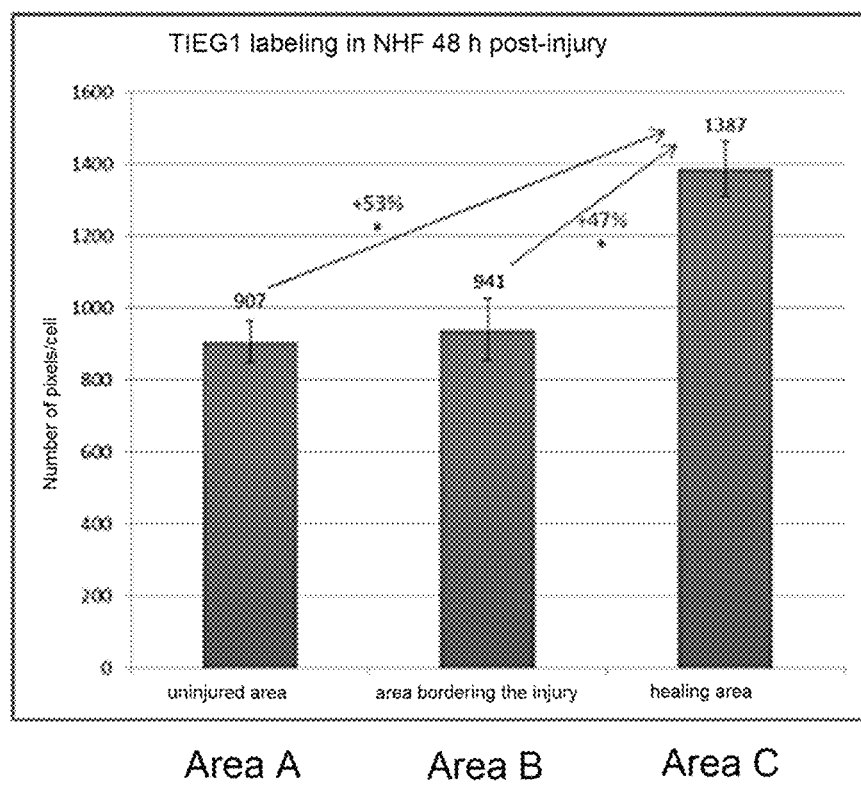

A: outside the injury
B: injury and outside the injury
C: injury

B

COSMETIC COMPOSITION COMPRISING ROYAL JELLY OF THE OUESSANT BLACK BEE

CROSS-REFERENCE TO RELATED APPLICATIONS

This application is a U.S. National Stage Application pursuant to 35 U.S.C. § 371 of International Patent Application PCT/EP2017/084402, filed on Dec. 22, 2017, and published as WO 2018/115448 on Jun. 28, 2018, which claims priority to French Patent Application 1663154, filed on Dec. 22, 2016, all of which are incorporated herein by reference in their entireties for all purposes.

The object of the present invention is a cosmetic composition promoting skin regeneration and/or healing comprising royal jelly from the Ouessant black bee (*Apis mellifera mellifera*) in a cosmetically acceptable medium.

Tissue healing and regeneration are complex, intimately linked processes which involve many cell types, multiple regulatory systems, complex cell communication, and the secretion of a large number of transcription factors (Martin, 1997).

TGF-beta (TGF-ß) is the main trigger and regulator of the three main stages of the healing process: inflammation, cell proliferation and tissue remodeling. Through its spectrum of activity and its actions upstream of this process, the TGF-ß pathway is the biological pathway that accelerates or, conversely, slows down the healing mechanisms.

TGF-ß acts by binding to its cell receptors forming a complex of type I (TßR-I) and type II (TßR-II) receptors and via the activation of the smad pathway, thus leading to a positive regulation of a set of genes. These TGF-ß-regulated genes are involved in the synthesis of extracellular matrix proteins, cell proliferation and motility, the downregulation of proteolytic enzyme expression, and the proliferation of dermal fibroblasts.

The TGF-ß pathway is altered by intrinsic aging and photoaging, leading to the skin thinning and delayed healing seen in the elderly, for example. Another feature of older skin is decreased collagen synthesis, which leads to skin thinning and increased fragility. However, a biological action to increase the production or concentration of TGF-ß to mitigate the effects of aging would be ineffective since it is an alteration of TGF-ß receptors that causes the loss of TGF-ß activity at the cellular and tissue level.

In addition, TIEG-1 (TGF beta early inducible gene 1) has been identified downstream of the TGF-ß pathway as a key factor in bone regeneration (Subramaniam M. et al. *Mol. Cell. Biol.*, 2005, 1191-1199), wound healing (Taguchi M. et al., *J. Musculoskelet. Res.*, 2008, 11, 63-69) but also the molecular organization of collagen fibers and the composition of the collagen matrix (Gumez L. et al., *J. Appl. Physiol.*, 2010, 108, 1706-1710).

Recent studies reported by Subramaniam M. et al. (*Biofactors*, 2010, 36, 8-18) have demonstrated the involvement of the gene encoding TIEG-1 in bone regeneration. Indeed, its expression is an element of the primary response of osteoblasts (cells synthesizing the non-mineral part of bones) to TGF-ß.

The identification of TIEG-1 protein, downstream of the TGF-ß pathway, is therefore a molecular target of interest to activate the TGF-β signaling pathway, particularly when TGF-ß receptors are altered.

In this context, the inventors have surprisingly shown that the expression of the TIEG-1 gene could be specifically increased under the effect of a novel cosmetic composition comprising royal jelly of the Ouessant (or Ushant) black bee (*Apis mellifera mellifera*). The inventors have also demonstrated that this composition could improve the regeneration of skin altered by intrinsic or extrinsic aging processes or by injury, for example by physical injury. The latter case relates to the healing process.

In particular, the inventors have shown that Ouessant black bee royal jelly can stimulate the expression of TIEG-1, and in particular within a healing area compared to a non-healing area.

Royal jelly is one of the products of beekeeping such as honey, propolis, pollen, bee venom and wax. However, these products are distinct from each other, both in terms of the way they are produced in the hive and in terms of their composition and properties.

Thus, honey is produced by bees that forage, collect nectar from flowers and produce it through successive digestion and regurgitation. The acid pH of the bees' stomachs, as well as the enzymatic activities of invertase, diastase and amylase, result in a supersaturated aqueous solution composed of 80% sugars, mainly fructose and glucose, with lower amounts of sucrose, maltose and other complex sugars.

Honey and pollen are substances that feed bees all year round, the former providing sugars and the latter proteins. Honey and pollen can be stored for long periods in the hive.

Workers are a category of bees that perform multiple tasks essential to the colony's maintenance and survival, while the queen and drones ensure the colony's reproduction. It is the workers who produce royal jelly from pollen and nectar collected by bees from flowers, royal jelly resulting from the secretion of their mandibular and hypopharyngeal salivary glands.

Royal jelly is the food of all hive larvae, without exception, for the first three days of their lives, and the exclusive food of the queen for the rest of her life. Due to its very complete composition, royal jelly provides all the nutrients necessary for larval growth and for the queen's equilibrium: a large quantity of water (between 60 and 70%), sugars (between 9 and 23%), proteins (between 10 and 18%) including a large proportion of amino acids, and lipids (between 4 and 8%). It is in the form of a gelatinous, white-yellow acid colloid and contains a specific fatty acid: 10-HDA (10-hydroxy-2-decenoic acid), identified as responsible for an important activity related to the development strategies of the colony.

Royal jelly is highly variable depending on the variety of bees and the environment in which they evolve.

The Ouessant black bee is a pure breed of a local ecotype of the west European black bee (*Apis mellifera mellifera*). The geographical location of the island of Ouessant, located more than 20 km off the coast of Finistère, constitutes an impassable barrier that has protected the Ouessant black bee from any hybridization with other bee species. Moreover, the island of Ouessant is an ecosystem that has always been protected, and this guarantees bees a healthy and diversified environment, which gives bees and their products unique features.

The object of the present invention is thus a cosmetic composition comprising Ouessant black bee royal jelly in a cosmetically acceptable medium.

While the use of Ouessant black bee honey in cosmetic compositions has been known for several years, it has never been considered to use Ouessant black bee royal jelly. They are in fact two different products, with different compositions and different properties.

Moreover, unlike "classic" royal jelly, which does not come from Ouessant black bees (*Apis mellifera mellifera*), Ouessant black bee royal jelly has the advantage of stimulating the expression of TIEG-1, particularly in the healing area, in an in vitro healing model by removing the cell monolayer and recolonization.

"Cosmetically acceptable" means that the composition is suitable for topical use, in contact with mammalian skin and more particularly human skin.

According to a preferred embodiment, the cosmetic composition according to the invention comprises Ouessant black bee royal jelly at a concentration comprised between 0.001% and 1%, preferably between 0.005% and 0.5%, and more preferably between 0.05% and 0.2% by weight of the total composition.

According to another object of the present invention, the cosmetic composition according to the invention is more particularly intended for skin regeneration and/or healing.

The composition of the invention is intended in particular for skin showing signs of chronological aging or photoaging.

Indeed, the intrinsic or extrinsic aging of the skin causes a slowdown in cell renewal and a degradation of the extracellular matrix to a greater extent than its neo-synthesis, which indicates a loss of skin homeostasis. This results in a thinning of the skin, a sagging of the skin, as well as the appearance of wrinkles and fine lines.

According to a preferred embodiment, the composition of the invention is intended for topical application.

The cosmetic composition according to the invention comprises, in addition to the Ouessant black bee royal jelly, one or more cosmetic excipients acceptable among those known to the skilled person in order to obtain a composition for topical application in the form of milk, cream, ointment, water-in-oil or oil-in-water emulsion, balm, gel, lotion, serum, spray, preferably cream or serum.

Depending on the nature of the composition, one or more cosmetically acceptable excipients will be selected from polymers, surfactants, rheology agents, fragrances, electrolytes, pH adjusters, antioxidants, preservatives, dyes, mother-of-pearl, pigments and mixtures thereof.

In a particular embodiment, the cosmetic composition according to the present invention may also comprise at least one cosmetically active agent well-known to the skilled person selected from agents to delay or slow the appearance of signs of intrinsic or extrinsic skin aging; agents having a skin depigmenting or lightening activity; agents having slimming activity; agents having moisturizing activity; agents having calming, soothing or relaxing activity; agents stimulating skin microcirculation to improve the radiance of the complexion, especially the face; agents having sebum-regulating activity for the care of oily skin; agents for cleaning or purifying the skin; agents having anti-radical activity.

The cosmetic composition of the invention may thus comprise one or more other substances that may be advantageously selected from:

molecules promoting cell renewal such as retinol and/or its esters; alpha- or beta-hydroxy acids such as fruit acids, particularly malic acid, glycolic acid or citric acid, salicylic acid or its esters, gentian acid or its esters, in particular tocopherol gentisate;

molecules or extracts stimulating skin firmness such as peptides stimulating collagen synthesis, in particular collagen type I, II, IV or VII, an extract of *Centella asiatica*, madecassic acid, asiatic acid, madecassoside, oat extracts, an extract of *Bertholletia excelsa*, a soy protein or peptide hydrolysate, an extract of *Potentilla erecta*, an extract of *Siegesbeckia orientalis*, ginsenosides or notoginsenosides, an *Albizia julibrissin* bark extract, a ursolic acid-rich extract of rosemary leaf, molecules or extracts promoting the synthesis of hyaluronic acid or glycosaminoglycans in the epidermis and dermis, such as an extract of Mamaku Vital Essence, a *Cyathea medullaris* leaf extract, an extract of *Eriobotrya japonica* or small hyaluronic acid fragments of low molecular weight or an extract of *Adenium obesum*;

molecules or extracts regulating epidermal differentiation such as ecdysterone, turkesterone, calcium derivatives, vitamin D precursors;

adenosine, carnitine or derivates thereof, in particular acetylcarnitine, cosmetically acceptable esters of retinol, in particular retinol propionate or palmitate;

metalloproteinase (MMP) inhibitors, in particular MMP 1, 2, 9 inhibitors such as an extract of *Ruscus aculeatus*, soy peptides or flavonoid extracts of plants containing them;

elastase inhibitors such as plant extracts of *Aspergillus fumigatus*, of *Momordica charantia*, of *Cucurbita maxima*;

an elastin-like peptide, advantageously esterified, such as that formed by the sequence palmitoyl-Val-Gly-Val-Ala-Pro-Gly marketed under the trade name BIOPEPTIDE EL by SEDERMA;

substances capable of stimulating dermatopontin synthesis, such as amber extract;

astringent plant molecules or extracts that tighten pores such as hamamelis extract; zinc gluconate filters protecting against UVA and UVB radiation, such as benzophenone 4-butyl methoxydibenzoylmethane, ethylhexyl methoxycinnannate, octocrylene, ethylhexyl salicylate, sulfonic acid phenylbenzymidazole, homosalate, alone or in combination with titanium oxides;

plant molecules or extracts acting on pigmentation such as kojic acid, liquorice or mulberry root extracts, arbutin, calcium pantothenosulfonate, boldine, diacetylboldine, vitamin C, or a derivative thereof, such as glycosides, lily extracts, in particular bulb extracts.

anti-free radical or anti-inflammatory molecules or extracts such as an extract of *Artemisia capillaris*, an extract of *Sanguisorba officinalis*, resveratrol and derivates thereof, cucurma, cucurmin or tetrahydrocucurmin, polyphenols extracted from grape seeds, vitamin E and derivates thereof, in particular phosphate derivatives thereof, ergothioneine or derivates thereof, idebenone;

an orchid extract such as an orchid belonging to the genus *Brassocattleya*, for example an extract of the orchid *Brassocattleya marcella*, or to the genus *Vanda*, for example an extract of an orchid among *Vanda coerulea*, *Vanda teres* and *Vanda denisoniana*;

moisturizing agents such as glycerol, trimethyl glycine or natural polyols, natural or synthetic ceramides, spring or mineral waters.

Advantageously, the composition according to the invention may also comprise honey or honey extract. The honey is preferably unifloral or polyfloral honey.

Preferably, the honey used in the composition according to the invention may be clover (*Trifolium repens*) honey, Ouessant honey, euphorbia honey (*Euphorbia echinus*) or Corsican honey.

Regardless of the form, the cosmetic composition of the invention is applied to a part of the skin of the body, in particular the face, neck, neckline and/or hands.

According to another aspect, the present invention relates to a cosmetic treatment process to stimulate skin regeneration and/or healing, characterized in that a sufficient amount of a cosmetic composition comprising Ouessant black bee royal jelly, as cosmetically active agent, is applied to the skin.

The following figures and examples are given by way of illustration and are not limiting.

FIGURES

FIG. 1: TIEG-1 protein expression in an in vitro healing model in NHF. A. Diagram of areas of interest where an immunofluorescent signal is quantified in a healing model. area A: remote from the injured area; area B: mixed area including the area bordering the wound and a control area on the cell monolayer; area C: wound area corresponding to the area scraped by a pipette tip; B. TIEG-1 protein expression in fibroblasts 48 hours after injury.

Figure 2:
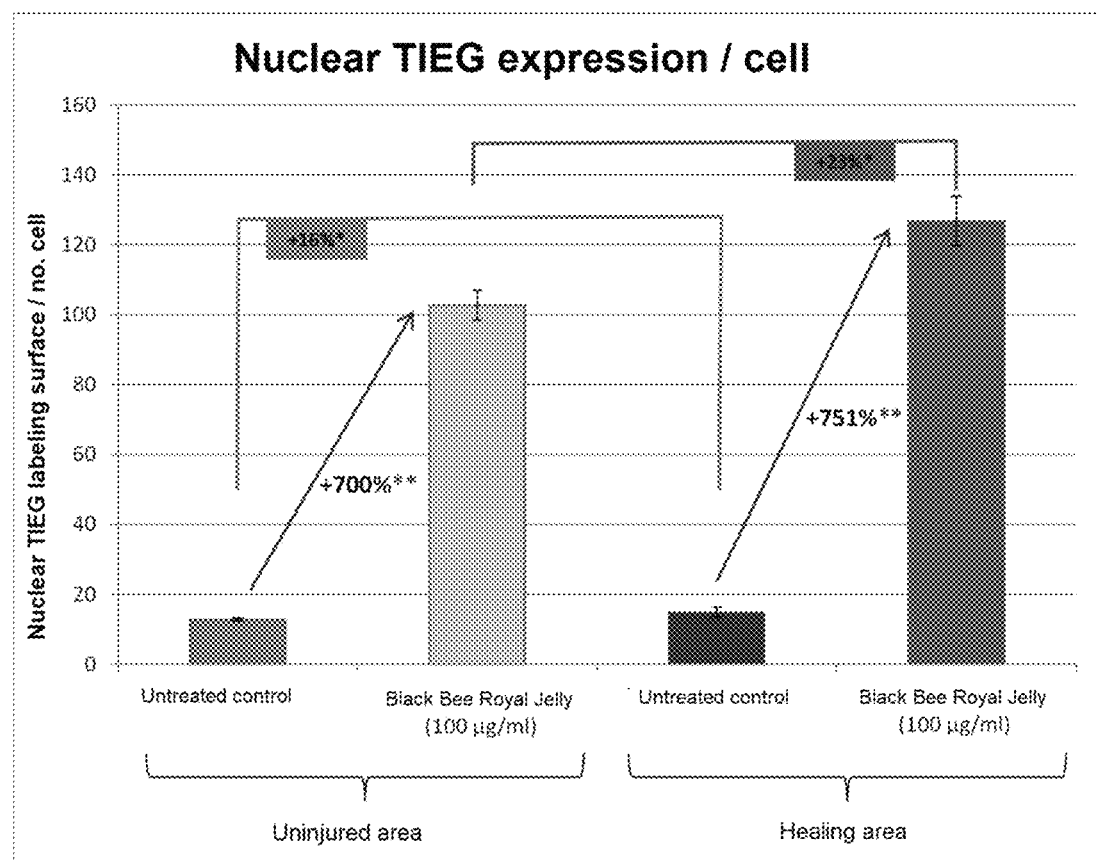

FIG. 2: Effect of Ouessant black bee royal jelly on the TIEG1 protein level in cultured NHF in injured (or healing) and non-injured areas.

Figure 3:
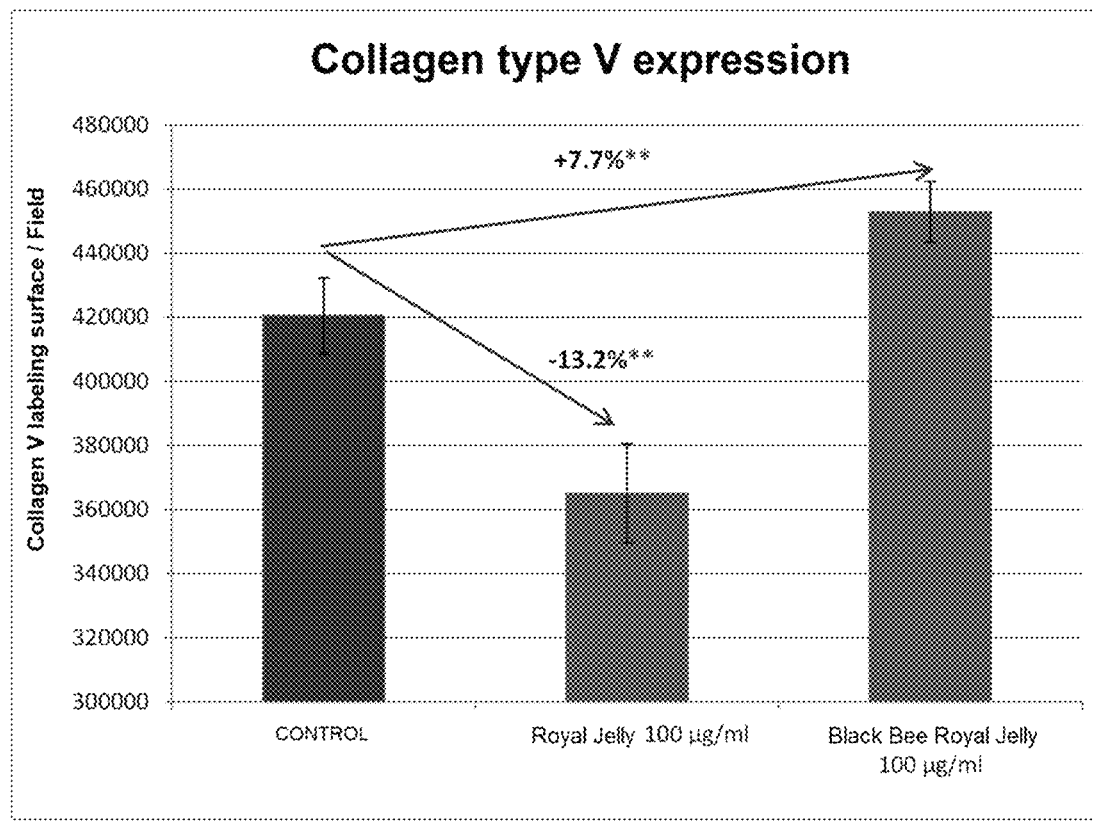

FIG. 3: Effect of Ouessant black bee royal jelly and Buckfast bee royal jelly on the synthesis of type V collagen in cultured NHF.

Figure 4:
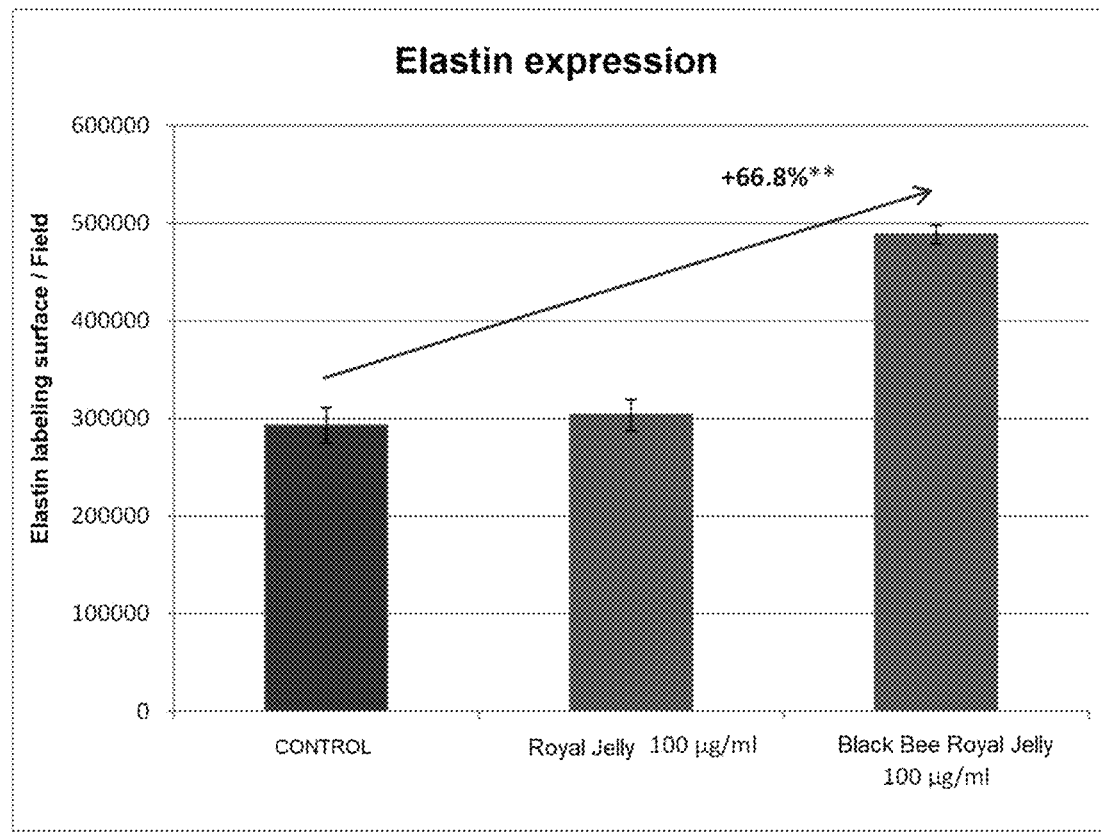

FIG. 4: Effect of Ouessant black bee royal jelly and Buckfast bee royal jelly on elastin synthesis in cultured NHF.

EXAMPLES

Example 1

Expression of TIEG-1 in an In Vitro Healing Model

Cell culture can be used to obtain a surface uniformly covered with cells. This cell monolayer can be injured and torn by scraping a pipette tip across its surface.

On this model, three different areas are distinguished: the wound area corresponding to the area scraped by the pipette tip (area C), a mixed area i.e. the area comprising the area bordering the wound (area B) and a control area on the cell monolayer, at a distance from the wounded area (area A) (FIG. 1, A). TIEG-1 expression was revealed by immunolabeling and quantified by image analysis in the fibroblasts present in these three areas when the healing process is initiated.

This study shows that TIEG-1 is significantly overexpressed in injury area C by 47% compared to mixed area B and 53% compared to control area A (FIG. 1, B).

This indicates that TIEG-1 has a major role in the mechanism of cell mobility, particularly fibroblastic, a major mechanism in the healing process.

Example 2

Effect of Ouessant Black Bee Royal Jelly on TIEG Protein Expression in Cultured Normal Human Fibroblasts (NHF) Subjected to a Healing Test TIEG 1 expression is evaluated under the effect of a treatment with Ouessant black bee royal jelly (0.01%) in an in vitro healing model of cultured NHF.

2.1. Cell Treatments

NHF from a 37-year-old Caucasian woman's abdominoplasty are seeded (80,000 cells per Petri dish) 35 ibidi treat in low-glucose DMEM medium implemented with 10% FBS and a mixture of antibiotics (penicillin/streptomycin) and maintained in culture for 48 hours, then the medium is changed and replaced by FBS-depleted medium. After 24 hours of culture without FBS, the NHF are treated with Ouessant black bee royal jelly at a dose of 100 µg/ml.

After 15 hours of treatment, the NHF monolayer of each Petri dish is injured using a cross-shaped pipette tip.

Twenty-four hours after the injury, the culture medium is removed and TIEG1 immunolabeling is performed.

The cells are fixed in formalin and then permeabilized with Triton (0.1%) for 10 minutes. They are then saturated with 1% phosphate-buffered saline (PBS)/bovine serum albumin (BSA) for 30 minutes. The primary antibody (rabbit anti-KLF10; Abcam) is diluted 1:200 in 1% PBS-BSA buffer and incubated on the cells at room temperature for 1 hour. After rinsing with PBS, the secondary antibody (Alexa Fluor® 568 Goat Anti-Rabbit IgG) is diluted 1:200 in 1% PBS-BSA buffer and deposited at room temperature for 1 hour in the dark. Labeling of nuclei with DAPI (diluted 1:100) and of actin filaments with phalloidin 488 (diluted 1:200) is carried out in parallel with the incubation of the secondary antibody.

After rinsing with PBS, a few drops of aqueous mounting medium are added. The dishes are finally stored at 4° C. waiting for image acquisition under a fluorescence microscope.

2.2. Image Acquisition and Analysis Under a Confocal Microscope

Images are taken with a Leica SP5 II confocal microscope with an ×20 air objective at 1024×1024 pixel resolution. Three images are taken in the uninjured area and three or more images in the injured area, with the same acquisition parameters. Images are taken after excitation of the fluorochromes by a specific laser: 1. argon laser (488 nm), 2. laser diode (405 nm) and 3. helium-neon laser (633 nm).

Once the acquisitions have been made, the images are analyzed one by one using Leica QWin software to obtain a quantitative description.

An image analysis program allows specific detection of nuclei and TIEG-1 labeling. The detection of TIEG-1 labeling is performed in the cytoplasmic compartment and in the nucleus of the cells. For each condition, the quantification of TIEG-1 is measured in the healing area and in the uninjured area. The values of this quantification are systematically weighted by the number of nuclei or cell surface area.

2.3 Results

The results (FIG. 2) are grouped in Table 1 below for the uninjured and injured areas (healing area).

TABLE 1

Nuclear expression of TIEG1 in the uninjured area and in the healing area treated with Ouessant black bee royal jelly or untreated.

|  | Treatment conditions | Nuclear TIEG expression/cell | |
|---|---|---|---|
|  |  | Mean | Standard deviation |
| Uninjured area | Control untreated | 12.9 | 0.6 |
|  | Ouessant black bee royal jelly (100 µg/ml) | 102.7 | 6.5 |
| Healing area | Control untreated | 14.9 | 2.1 |
|  | Ouessant black bee royal jelly (100 µg/ml) | 126.8 | 12.5 |

Ouessant black bee royal jelly induces a significant increase in the nuclear expression of TIEG1 compared to the untreated control by +700% in the uninjured area and +751% in the healing area (FIG. 2).

In addition, it is noted that treatment with Ouessant black bee royal jelly increases TIEG1 expression in the nuclear compartment of cells in the healing area by 23% compared to the expression of TIEG-1 after treatment of cells in the uninjured area, compared to 16% for the untreated control.

Thus, treatment with Ouessant black bee royal jelly acts more effectively on a healing area, which makes it particularly attractive for use as an anti-aging agent in cosmetic skin care compositions designed to prevent or slow the appearance of signs of intrinsic or extrinsic skin aging.

Example 3

Study of the Effect of Ouessant Black Bee Royal Jelly and Buckfast Bee Royal Jelly on the Expression of Collagen V and Elastin in Cultured Normal Human Fibroblasts (NHF)

3.1 Cell Treatments

NHF are seeded in T75 vials (75 cm$^2$ flask, BD Biosciences) in Dulbecco's modified Eagle's medium (DMEM) supplemented with 10% fetal calf serum.

The NHF are trypsinized at confluence with 0.05% trypsin-EDTA solution and neutralized with medium containing serum. Then they are seeded in 2 24-well plates at 38,000 cells per well.

The NHF are then optionally treated with royal jelly of the Ouessant black bee or of the Buckfast bee tested at 100 µg/ml concentrations for 6 days. The Buckfast bee is a cross between the bee subspecies *Apis mellifera mellifera* and *Apis mellifera ligustica*. The treatment is performed twice for each condition and repeated 3 times during these 6 days. For the untreated (UT) control conditions, the medium is replaced by new medium.

After 6 days of treatment, the cells are rinsed twice with phosphate buffer, then fixed in formalin (10% solution) for 10 minutes. After 2 rinses with PBS, the cell membranes are permeabilized with 0.1% PBS/Triton X-100 solution (Sigma), then rinsed twice with phosphate buffer.

The cells are covered with 1% bovine serum albumin solution in phosphate buffer for 30 minutes at room temperature.

The PBS/BSA solution is then replaced by a primary antibody solution corresponding to each labelled protein (see Table 2 below) diluted 1:100 in 1% PBS/BSA.

TABLE 2

Summary of antibodies used

|  | Primary Antibody | Secondary Antibody |
|---|---|---|
| Collagen V | Novotec 20511, Rabbit 1:500 | Alexa Fluor 568 Goat Anti Rabbit (Molecular Probes) 1:200 |
| Elastin | Novotec 25011, Rabbit 1:200 |  |

The plates are incubated for 2 hours at room temperature.

The cells are then rinsed with phosphate buffer and covered with a solution of secondary antibody according to the primary antibody to be targeted (Table 2) and DAPI (4',6'-diamidino-2-phenylindole, dihydrochloride) diluted respectively 1:200 and 1:100 in 1% bovine serum albumin solution in 1% phosphate buffer. The plates are stored for one hour in the dark and at room temperature.

The secondary antibody solution is then aspirated, and the cells rinsed with PBS and then distilled water. A few drops of mounting medium (Aqua-Mount, Lab Vision Thermo Scientific) are deposited in each well.

3.2. Image Acquisition and Analysis by High-Content Screening (HCS)

The plates are scanned with the "ArrayScan XTi" (Thermo Cellomics).

Acquisition conditions:
Detection:
DAPI: filter XF53_386_23
Alexa Fluor 568: filter XF53_572_15
Resolution: 1104×1104
Objective: 10× dry
Number of images: 49 per well (i.e. 2×49=98 per condition)

The images are analyzed using the Spot Detector image analysis software, which detects the red labeling of the target protein, corresponding to its expression. The surface of the measurement area corresponds to the entire surface of the image. The number of cells is determined by counting the nuclei by detecting the blue labeling.

3.3. Results a. Type V Collagen Expression

Ouessant black bee royal jelly significantly increases the synthesis of type V collagen on NHF compared to the untreated control (FIG. 3).

Ouessant black bee royal jelly also has a significantly higher effect than that observed for Buckfast bee royal jelly (FIG. 3).

b. Elastin Expression

Ouessant black bee royal jelly more significantly increases (+66.8%) elastin synthesis on NHF (FIG. 4).

The results obtained on different targets involved in the synthesis of the extracellular matrix in NHF show that Ouessant black bee royal jelly has an activating effect on the expression of type V collagen and elastin, which is significantly higher than that measured for Buckfast bee royal jelly. No particular effects on the expression of type V collagen and elastin are observed in NHF treated with Buckfast bee royal jelly.

On the contrary, Buckfast bee royal jelly showed that it significantly decreased (−13.2%) the synthesis of type V collagen on NHF compared to the untreated control.

Example 4

SPF 15 Day Cream

The composition below is an oil-in-water emulsion.

Ouessant black bee royal jelly is identified by a high 10-hydroxy-2-decenoic acid content compared to the content of that compound in a Buckfast bee jelly.

Percentages are expressed by weight with respect to the final composition:

| | |
|---|---|
| Ouessant black bee royal jelly | 0.01 |
| Octocrylen | 2.0 |
| Octyl methoxycinnate | 7.5 |
| Ethyl 2 hexyl palmitate | 4.0 |
| Phenyl trimethicone | 0.5 |
| Glyceryl monostearate | 0.2 |
| Cetearyl alcohol/dicetylphopshate/ceteth-10 phosphate | 2.0 |
| Glyceryl stearate/PEG-100 stearate | 2.0 |
| Cetyl alcohol | 2.0 |
| Beeswax Polyglyceryl-3 | 0.4 |
| Benzophenone-3 | 1.5 |
| Caprylic/caric triglyceride | 3.5 |
| Butylene glycol dicaprylate/dicaprate | 2.5 |
| C12-15 alkyl benzoate/titanium dioxide/polyhydroxystearic acid/aluminum stearate/alumina | 2.5 |
| Sodium polyacrylate | 0.6 |
| Butylene glycol | 2.0 |
| Diglycerin | 1.0 |
| Glycerol | 3.5 |
| Sodium hyaluronate | <0.1 |
| Xanthan gum | 0.2 |
| Ammonium acryloyldimethyltaurate/VP copolymer | 0.4 |
| Citric acid | <0.1 |
| Trisodium citrate | 0.1 |
| Aluminum starch octenylsuccinate | 1.5 |
| Rosemary leaf extract solution | 2.0 |
| Silk tree bark extract solution (PRODIZIA ®) | 2.0 |
| Tocopheryl acetate | 0.2 |
| Adjuvants (fragrances, alkalinizers, preservatives) | qs |
| Purified water | qs 100 |

Ouessant black bee royal jelly is a paste that is dissolved in the continuous aqueous phase of the cream.

Each phase is prepared separately and then the fat phase is added under stirring in the aqueous phase in order to obtain a homogeneous dispersion of fat phase droplets in the continuous phase.

The cream has a particularly pleasant texture when applied. It is applied upon awakening, on the face, by a light massage, focusing on areas showing signs of aging such as wrinkles or fine lines or areas with sagging skin.

REFERENCES

*Biofactors,* 2010, 36, 8-18)
Gumez L. et al., *J. Appl. Physiol.,* 2010, 108, 1706-1710
Paul Martin, *Wound Healing-Aiming for Perfect Skin Regeneration, Science,* 1997, 276, 5309, pp. 75-81.
Snyder L. R. *Journal Of Chromatography,* vol. 92, 1974, pages 223-230
Subramaniam M. et al. *Mol. Cell. Biol.,* 2005, 1191-1199
Subramaniam M. et al., *Biofactors,* 2010, 36, 8-18
Taguchi M. et al., J. *Musculoskelet. Res.,* 2008, 11, 63-69

The invention claimed is:

1. A cosmetic composition comprising royal jelly of the Ouessant black bee in a cosmetically acceptable medium, wherein:
    said royal jelly is at a concentration between 0.001% and 1% by weight of the total composition, and
    said composition further comprises one or more cosmetically acceptable excipient selected from the group consisting of: polymers, surfactants, rheology agents, fragrances, electrolytes, pH adjusters, antioxidants, preservatives, dyes, mother-of-pearl, pigments, and mixtures thereof, and
    said cosmetic composition is in the form of an oil-in-water emulsion or a water-in-oil emulsion.

2. The cosmetic composition of claim 1, wherein said royal jelly is at a concentration between 0.005% and 0.5% by weight of the total composition.

3. The cosmetic composition of claim 1, wherein said royal jelly is at a concentration between 0.05% and 0.2% by weight of the total composition.

4. A method for stimulating skin regeneration and/or healing comprising the administration of an effective amount of the cosmetic composition of claim 1 to a patient in need thereof.

5. The cosmetic composition of claim 1, further comprising unifloral or polyfloral honey or honey extract.

6. The cosmetic composition of claim 1, further comprising clover (*Trifolium repens*) or *euphorbia* honey.

* * * * *